US011137392B2

(12) United States Patent
Ndieyira et al.

(10) Patent No.: US 11,137,392 B2
(45) Date of Patent: *Oct. 5, 2021

(54) CANTILEVER SENSORS FOR MOLECULE DETECTION

(71) Applicant: 3P SENSE LIMITED, London (GB)

(72) Inventors: Joseph Wafula Ndieyira, London (GB); Samadhan Patil, Glasgow (GB); Giuseppe Mazza, London (GB); Massimo Pinzani, London (GB)

(73) Assignee: 3P SENSE LIMITED, London (GB)

( * ) Notice: Subject to any disclaimer, the term of this patent is extended or adjusted under 35 U.S.C. 154(b) by 21 days.

This patent is subject to a terminal disclaimer.

(21) Appl. No.: 16/593,477

(22) Filed: Oct. 4, 2019

(65) Prior Publication Data

US 2020/0033329 A1    Jan. 30, 2020

Related U.S. Application Data

(62) Division of application No. 15/191,056, filed on Jun. 23, 2016, now Pat. No. 10,458,980.

(51) Int. Cl.
*B81B 3/00* (2006.01)
*G01N 33/53* (2006.01)
(Continued)

(52) U.S. Cl.
CPC ....... *G01N 33/5306* (2013.01); *C23C 14/021* (2013.01); *C23C 14/025* (2013.01);
(Continued)

(58) Field of Classification Search
CPC .... G01N 33/53; G01N 33/5306; G01N 33/50; G01N 33/48; C23C 14/021; C23C 14/02; C23C 14/025; C23C 14/024; B81B 3/00
(Continued)

(56) References Cited

U.S. PATENT DOCUMENTS

| 2014/0127822 A1* | 5/2014 | Arora ............... G01N 33/0057 436/98 |
| 2016/0038546 A1 | 2/2016 | Biava | |

OTHER PUBLICATIONS

Berger, Surface Stress in Self-Assembly of Alkanethiols on Gold, Science, 276, 5321, Jun. 27, 1997, p. 2021-2024. (Year: 1997).*
(Continued)

*Primary Examiner* — Christine T Mui
(74) *Attorney, Agent, or Firm* — Jeffrey N. Townes; Cozen O'Connor

(57) ABSTRACT

A method of preparing a cantilever sensor for measuring biochemical interactions and their associated stress wherein a cantilever having two sides is coated on one side with at least a gold layer and both sides of the cantilever are functionalized with a self-assembled monolayer (SAM) of a probe molecule by incubating the cantilever in a solution having a concentration of the probe molecule of between 1 to 1000 μM. The unpassivated cantilever sensor comprising a layer coated on one side with a coating comprising gold and being unpassivated on the opposite side, wherein both surfaces comprises a self-assembled monolayer of a probe molecule in which the surface area occupied per probe molecule varies in the range 0.4-1.5 nm², enabling the stress at the gold top surface that is not cancelled out by a counter stress from the bottom surface so that accurate quantitation of a target molecule is achieved.

21 Claims, 5 Drawing Sheets

(51) Int. Cl.
| | |
|---|---|
| *C23C 14/02* | (2006.01) |
| *C23C 14/16* | (2006.01) |
| *C23C 14/30* | (2006.01) |
| *C23C 14/58* | (2006.01) |
| *C23C 26/00* | (2006.01) |
| *G01N 33/543* | (2006.01) |
| *G01N 33/552* | (2006.01) |
| *G01N 33/553* | (2006.01) |

(52) U.S. Cl.
CPC .............. *C23C 14/16* (2013.01); *C23C 14/30* (2013.01); *C23C 14/58* (2013.01); *C23C 26/00* (2013.01); *G01N 33/5308* (2013.01); *G01N 33/54373* (2013.01); *G01N 33/54393* (2013.01); *G01N 33/552* (2013.01); *G01N 33/553* (2013.01); *G01N 2333/51* (2013.01)

(58) Field of Classification Search
USPC ........................................ 436/63; 73/862.634
See application file for complete search history.

(56) References Cited

OTHER PUBLICATIONS

Lang et al., "Nanomechanical Cantilever Array Sensors," Springer Handbook of Nanotechnology, 427-452 (2010).
Pham et al., "Surface modification of a gold-coated microcantilever and application in biomarker detection," Adv. Nat. Sci.: Nanosci. Nanotechnol. 6: 1-8 (2015).
Rastegar et al., "Nanomechanical Actuation of a Silicon Cantilever Using an Azo Dye, Self-Assembled Monolayer," Langmuir: 29: 7118-7124 (2013).
Patil et al., "Decoupling competing surface binding kinetics and reconfiguration of receptor footprint for ultrasensitive stress assays" and supplemental materials, Nature Nanotechnology 10: 899-908 (2015).
Fritz et al., "Translating Biomolecular Recognition into Nanomechanics", Science 288: 316-318 (2000).
Wu et al., "Bioassy of prostate-specific antigen (PSA) using microcantilevers", Nature Biotechnology 19: 856-860 (2001).
Backmann et al., "A label-free immunosensor array using single-chain antibody fragments", PNAS 102: 14587-14592 (2005).
Mukhopadhyay et al., "Cantilever Sensor for Nanomechanical Detection of Specific Protein Conformations", Nano Letters 5: 2385-2388 (2005).
Shu et al., "DNA Molecular Motor Drive Micromechanical Cantilever Arrays", J. Am. Chem. Soc. 127: 17054-17060 (2005).
Zhang et al., "Rapid and label-free nanomechanical detection of biomarker transcripts in human RNA", Nature Nanotechnology 1: 214-220 (2006).
Ndieyira et al., "Nanomechanical detection of antibiotic-mucopeptide binding in a model for superbug drug resistance", Nature Nanotechnology 3: 691-696 (2008).
Ndieyira et al., "Surface-stress sensors for rapid and ultrasensitive detection of active free drugs in human serum" Nature Nanotechnology 9: 225-232 (2014).

\* cited by examiner

CANTILEVER SENSORS FOR MOLECULE DETECTION

RELATED APPLICATION

This application is a Divisional Application of U.S. patent application Ser. No. 15/191,056, filed Jun. 23, 2016, now U.S. Pat. No. 10,458,980, which is herein incorporated by reference in its entirety.

TECHNICAL FIELD

The present invention relates to cantilever sensors and cantilever sensor arrays having enhanced selectivity and sensitivity for the detection of molecules in body fluids.

BACKGROUND ART

Cantilever sensors have attracted considerable attention over the last decade because of their potential as a highly sensitive sensor platform for high throughput and multiplexed detection of proteins, nucleic acids and other molecules.

Biological specificity in detection is typically achieved by immobilizing selective receptors or probe molecules on one side of the cantilever using surface functionalization processes.

Biomolecular interaction between the immobilized receptors or probes and a coupling molecule in a body fluid causes a measurable bending of the cantilever. This nanoscale deflection is caused by a variation in the cantilever surface stress due to the biomolecular interaction and can be measured by optical or electrical means, thereby reporting on the presence of specific molecules and their quantitation in the body fluid.

The cantilever bending is a function of the number of molecules bound to the probe molecules on its surface.

Biosensing technologies based on cantilever arrays have the potential of satisfying the need for multi-target detection with high sensitivity and selectivity using very small volumes of sample.

When cantilevers are made softer with very small force constants, they can measure forces and stresses with extremely high sensitivity.

The very small force constant (typically less than 0.01 N/m) of a cantilever allows detection of surface stress variation due to the adsorption (or specific surface-receptor interaction) of molecules.

Known cantilever sensors are typically made of rectangular silicon, or polyamide polymer materials coated with a layer of gold on one side (the top surface) and with non-reactive layer of molecules such as PEG-silane on the other side (the bottom surface). The PEG-silane coating of the bottom surface is called passivation layer. The purpose of passivation of the bottom surface is to help avoiding unwanted functionalization of the bottom surface with receptors or probe molecules, consequently preventing probe molecule (ligand) adsorption that would alter sensing results. Receptors or probe molecules are typically immobilized on the cantilever top gold surface using, for example, alkanethiol chemistry.

The need for mass-produced, miniature microcantilever arrays having unprecedented sensitivity for label-free bio-detection applications, such as toxin, protein, drugs and antibody detection, DNA hybridization, selective detection of pathogens etc. is significant. However, improvements in cantilever sensitivity and selectivity are far from finished and there is still a long felt need in the sector of label-free molecular detection.

Passivating of the underside of the cantilever to prevent unwanted ligand adsorption is lengthy and often requires tedious optimization. For example, on average more than 60 minutes is necessary to passivate a single micro-cantilever array with PEG-silane. Moreover, the detailed investigation of Si surface passivation shows that the process of cantilever underside coating to prevent unwanted adsorptions is far from complete and therefore needs further optimization.

Therefore, it would be desirable to provide cantilever sensors without the need of a passivation layer but, at the same time, having the same or even an enhanced selectivity and sensitivity with respect to the known passivated cantilevers.

SUMMARY OF THE INVENTION

The present invention refers to a process for immobilizing probe molecules (such as receptors or antibodies) able to interact with a ligand or drug molecule on nanomechanical cantilevers so that they can function, in a reliable, selective and sensitive way, without the need to passivate the underlying surface.

By tuning the probe molecule concentration (i.e. by working in a concentration range of 1 to 1000 μM), the impact of the underlying surface SAM functionalization can be minimized.

Moreover, the area per probe molecule (i.e. the probe molecule spacing) on the cantilever surface influences coupling molecule/probe molecule binding and can affect the mechanical stress and hence on the sensitivity and selectivity of the sensor.

The process of the disclosure therefore yields a cantilever having the same or even an enhanced selectivity and sensitivity with respect to the known passivated cantilevers without the drawbacks of the passivation procedure (which is lengthy and often requires tedious optimization).

In another aspect, the disclosure provides a method for detecting molecules in body fluids having improved selectivity and sensitivity.

DETAILED DESCRIPTION OF THE DISCLOSURE

Figure 1A:
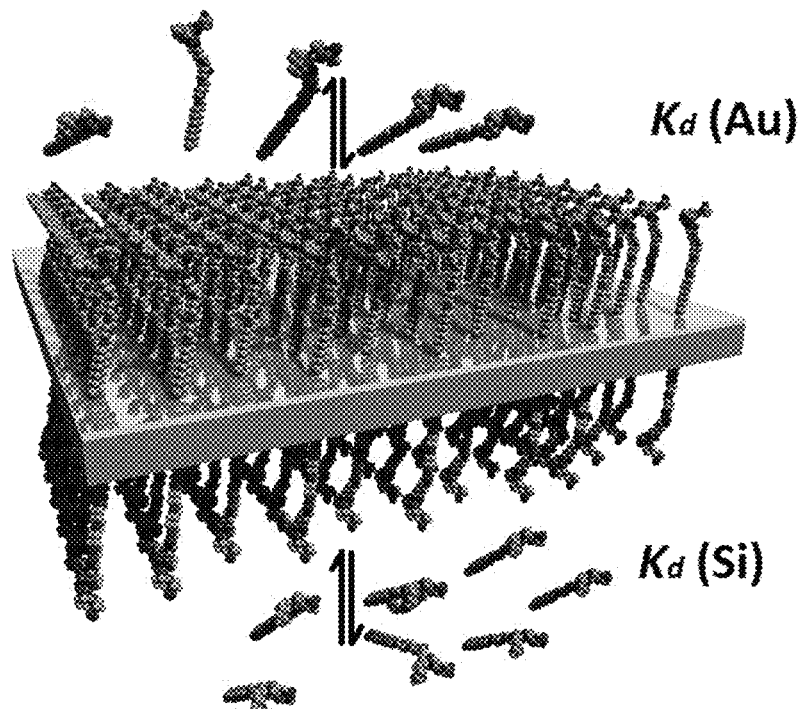
FIGS. 1a-b show the functionalization of both surfaces of the cantilever with a self-assembled monolayer (SAM) of vancomycin (Van) susceptible receptor (VSR ~0.6 kDa) analogues of the bacterial cell wall precursors that present uncrosslinked peptide motifs terminating in the sequence lysine-D-alanine-D-alanine.

The process of preparation of an unpassivated cantilever comprises the steps of:
1) Providing a microcantilever sensors having two sides;
2) Coating one side of the cantilever with at least a gold layer;
3) Functionalizing both sides of the cantilever with a self-assembled monolayer (SAM) of a probe molecule by incubating the cantilever in a solution having a concentration of the probe molecule of between 1 to 1000 µM.

The cantilever sensor used in the present process is preferably included in an array comprising at least eight cantilevers. In a preferred embodiment, the process of the disclosure is a process of preparation of an array of unpassivated cantilever, preferably an array of at least eight unpassivated cantilever.

Preferably, the cantilever of the disclosure has a rectangular shape. Typical sizes of the cantilever sensor are: 500 µm long, 100 µm wide and 1 µm thick.

The coating of one side of the cantilever with at least a gold layer preferably includes the deposition of a first (or base) titanium layer (called the adhesion layer) and then of a top gold layer.

The coating of step b) is achieved by using any method known in the art. Preferably, the Au coating is prepared by using any of the known physical thermal vapor deposition (PVD) methods (for example, the thermal evaporation technique) or any of the known PVD techniques, such as the electron beam evaporation technique.

Metal coating preparation includes deposition of a first titanium layer followed by deposition of a gold layer under vacuum until the desired thickness is achieved. Typically, the thickness of the titanium layer is between 1 and 5 nm. The thickness of the gold layer is typically between 5 and 30 nm, preferably between 10 and 20 nm.

Self-assembled monolayer (SAM) refers to organic molecule assemblies that form spontaneously on surfaces (for example by adsorption) and are organized into more or less large ordered domains. Typically, molecules that assemble into monolayer possess a head group that has a strong affinity to the surface and anchors the molecule to it, a tail and an end functional group. Common head groups include thiols, silanes, phosphonates, etc.

The self-assembled monolayer of the disclosure preferably is an alkanethiol self-assembled monolayer in which the alkanethiol moiety is the linker between the probe molecule (i.e. functional group) and the Au and/or Si surface, as depicted below:

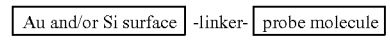

Preferably, the alkanethiol linker is an alkanethiol polyethylene glycol moiety.

The linker interacts with the Au and/or Si surface through the terminal —SH residue and is covalently attached to the probe molecule through the —OH group of the polyethylene glycol moiety. The interaction between the Au and/or Si surface and the alkanethiol linker is a semi-covalent type of interaction due to the strong affinity of sulfur for these metals.

In a preferred embodiment, the alkanethiol linker is $HS(C_{8-15})alkyl-(OCH_2CH_2)_nOH$, wherein n=2-5.

Preferably, the alkanethiol linker is $HS(OCH_2CH_2)_3OH$, that binds to the Au and/or Si surface of the cantilever via the —SH residue and to the probe molecule via the —OH group, as depicted below:

The probe molecule can be any molecule able to interact with specificity and sensitivity with another molecule (a coupling molecule), thus generating ligand-receptor or drug-receptor or sequence-specific DNA or RNA hybridization-type interactions or antibody-antigen interactions.

The probe molecule preferably is a receptor able to provide ligand-receptor or drug-probe binding or a probe molecule able to selectively hybridize to a complementary DNA or RNA sequence or an antibody able to provide antibody-antigen interaction.

For example, the receptor is selected from: the vancomycin susceptible receptor (VSR), monoclonal human immunodeficiency virus antibody (anti-p24), factor (VIII) antibody (anti-Factor (VIII)), polyclonal anti-prostate-specific antibody (anti-PSA), or combinations thereof.

The coupling molecule is a ligand, a drug molecule, a protein, an antigen, a hybridizing nucleic acid sequence, or combinations thereof. For example, the coupling molecule is vancomycin, glycoprotein p24, factor (VIII) and prostate specific antigen (PSA).

The probe molecule is attached with the linker, preferably an alkanethiol linker, prior to the preparation of the incubating solution.

A solution of the probe molecule bound to the linker is prepared by diluting the molecule in an organic solvent solution (such as ethanol or methanol solution) to yield a concentration of probe molecule of 1 to 1000 μM, preferably 30 to 100 μM, more preferably 20 to 60 μM, even more preferably about 50 μM. The cantilever is incubated in the solution for 10-60 minutes, preferably from 10-30 minutes and in any case until a SAM is formed.

By working in the probe molecule concentration of 1 to 1000 μM, a surface area occupied on the Au side per probe molecule of 1.5 to 0.4 nm$^2$, preferably of 0.5 to 0.6 nm$^2$ is obtained and approximately 4.7 to 1.6 nm$^2$ in case of Si underside. Higher values of surface area for probe molecule (such as 1.6 or 0.6 nm$^2$) are obtained when lower concentrations of probe molecule are used, i.e. when the probe molecule concentration is below 50 μM. Lower values of surface area per probe molecule (such as 0.4-0.5 nm$^2$) are obtained when higher concentrations of probe molecule are used, i.e. when the probe molecule concentration is 50 μM. The area per probe molecule achieves the highest values when the probe molecule concentration is between 30 and 100 μM, preferably between 20 to 60 μM, more preferably around about 50 μM.

By working in the above ranges of probe molecule concentrations, an area per probe molecule on the cantilever Au side of 0.4 to 1.5 nm$^2$, preferably of 0.5 to 0.6 nm$^2$, is achieved, which yields a compressive stress of the cantilever (in the presence of a coupling molecule to be detected in a body fluid) of 40 to 60 mN m$^{-1}$. This range of compressive stress is approximately twice more sensitive than the one obtained from the known cantilever (about 33 mN m$^{-1}$).

The area per probe molecule is calculated using X-ray photoelectron spectroscopy (as described in the example section of this disclosure).

Working in the range of the probe molecule concentrations in solution described above allows minimizing the amount of SAM that is formed on the Si bottom side of the cantilever consistent with their negligible impact on cantilever stress. Accordingly, the influence of the negative contributions of the interaction between the SAM formed on the Si side of the cantilever and the coupling molecule to the overall stress signal is minimized. Besides being a minimized influence, the negative contribution to the stress signal can be taken into account in order to calculate the net change in stress, which can thus be correlated in a reliable manner to the concentration of the coupling molecule to be detected in a body fluid.

The inventors of the present disclosure have devised a mathematical formula (1) to represent the simultaneous interactions at the Au and Si surfaces, where the surface stress is defined by coupling molecule/probe molecule complex interactions.

The net change in stress is expressed as:

$$\Delta\sigma_{eq} = \sigma_{max}(Au)\left(\frac{[Ligand]^n}{K_d^n(Au) + [Ligand]^n}\right) + \sigma_{max}(Si)\left(\frac{[Ligand]^m}{K_d^m(Si) + [Ligand]^m}\right) \quad (1)$$

where the first and second terms quantify the stress changes at the Au surface and Si surface, respectively. For the associated stress to cause an effective cantilever downward bending (compressive) with inclusion of the bound complex, the Au top expands, meaning the underlying Si surface undergoes contraction (tensile). Alternatively, other models known to one skilled in the art may be used.

In formula (1), the constants $\sigma_{max}(Au)$ and $\sigma_{max}(Si)$ are the maximum stresses when all accessible binding sites on the surfaces are fully occupied.

$K_d(Au)$ and $K_d(Si)$ are the equilibrium dissociation constants for the Au and Si surfaces, respectively, and n and m are the stoichiometric coefficients of the reactions.

It has been found that the equation formula (1) is a good mathematical model to calculate the net change in stress (and accordingly the concentrations of the ligand/drug molecule that is to be detected) when the starting concentrations of the probe molecule in solution is between of 1 to 1000 μM, preferably 30 to 100 μM, more preferably 20 to 60 μM, even more preferably about 50 μM. Indeed, it has been found that the value of $K_d(Au)$ correspond to the value of $K_d(Au)$ obtained from a model simulating a cantilever in which there is no free available Si bottom surface, only when working in the above probe molecule solution concentrations. Instead, it was found that $K_d(Au)$ increases by more than an order of magnitude when the probe molecule concentration is below 1 μM or greater than 1000 μM. The increase in $K_d(Au)$ at low probe molecule concentration, is due to the small net cantilever stress signal contribution from both surfaces, for the reason that a complete monolayer is not formed at this concentration. Conversely, when the probe molecule concentration is greater than 1000 μM, a large contribution from Si reactions comparable to that from the Au top surface obtained, results in a reduction in the net stress signal.

Thus, when either the probe molecule concentration is too low or higher than 1000 μM, the extracted $K_d(Au)$ values are artifacts. Consequently, a sufficient equilibrium net stress signal $\Delta\sigma_{eq}$ is desired for accurate binding analysis.

These findings demonstrate that the unpassivated cantilever of the present disclosure possess superior performance in terms of detection sensitivity and specificity only when the starting probe molecule concentration in solution is included in the above ranges.

It has also been found that stress generation efficiency (and therefore the cantilever sensitivity and selectivity) is also influenced by the probe molecule spacing on the cantilever surfaces. In particular, it has been found that, depending on the size of the incoming ligand or drug, the spacing must be tuned to allow perfect matching. When the incoming ligand to be detected is a small molecule, such as an antibiotic, then a smaller spacing between the probe molecules can be utilized to create good matching between probe molecule/coupling molecule. In contrast, for large molecules such as proteins, the probe molecule spacing must be large in order to enable matching to incoming coupling molecules. This means that in order to get large stress signal useful for sensitive and specific sensing, the probe molecule spacing may be adjusted to obtain perfect matching between a probe molecule and a coupling molecule. There is no standard probe molecule spacing that is universal for all coupling molecules.

It has been found that when the coupling molecule to be detected is a small molecule, the surface area occupied on the cantilever Au side per probe molecule is typically in the range 0.4-1.5 nm$^2$, preferably 0.5-0.6 nm$^2$ in order for the cantilever to possess good sensitivity and selectivity. When the molecule to be detected is a large molecule, such as a protein, the surface area per probe molecule is typically in a preferred range 0.6-1.2 nm², in order for the cantilever perform at best.

It is to be noted that these values of surface area per probe molecule are consistent with the surface coverage values obtained when working with a probe molecule concentration in solution comprised between 1 to 1000 µM, preferably 30 to 100 µM, more preferably 20 to 60 µM, even more preferably about 50 µM (which allow minimizing the quantity of probe molecule on the cantilever Si surface).

The present disclosure refers also to an unpassivated microcantilever sensor comprising a range of materials including silicon layer coated on one side (or surface) with a coating comprising Au and being uncoated or unpassivated on the opposite side (or surface). The Au coated surface is further coated with a self-assembled monolayer of a probe molecule, wherein the surface area occupied per probe molecule is in the range 0.4-1.5 nm², preferably 0.5-0.6 nm² or 0.6-1.2 nm² according to the size of the molecule to be detected. The probe molecule is able to bind in a selective way to the molecule to be detected in a body fluid, thereby forming a complex that causes bending of the cantilever. Bending of the cantilever generates a stress response that can be detected and correlated to the molecule concentration in the body fluid.

The cantilever coating comprising Au can also comprise a first layer of titanium (called adhesion layer) on top of which the Au layer is deposited.

The thickness of the titanium layer is between 1 and 5 nm. The thickness of the gold layer is between 5 and 50 nm, preferably between 10 and 20 nm.

The cantilever sensor of the present disclosure is preferably included in a sensor array comprising at least 8 unpassivated cantilevers, although less or longer more unpassivated cantilevers can be used.

The probe molecule and the self-assembled monolayer are as described above.

The cantilever of the disclosure is able to detect the presence of a molecule in a body fluid with femtomolar sensitivity.

The present disclosure refers also to a method for detecting the presence of a ligand/drug molecule in an ex-vivo body fluid, such as blood, plasma, urine, saliva, sweat or sputum (or combinations thereof), comprising the steps of:
1) Providing an unpassivated cantilever sensor according to the present disclosure;
2) Contacting the cantilever with a body fluid containing the molecule to be detected;
3) Detecting the response signal due to cantilever bending;
4) Correlating the response signal to the presence or absence of the molecule to be detected and, in case of presence, to the concentration of the molecule in solution.

The unpassivated cantilever sensor can be an array of at least 8 unpassivated cantilevers or more.

The contact between the cantilever and the body fluid of step 2) is performed for a period of about 5-30 mins, although shorter or longer times can be used.

During the contact, the probe molecule selectively binds to the molecule to be detected via a receptor-ligand, receptor-drug, antibody-antigen or hybridizing sequence-type of interaction, thereby forming a complex that causes mechanical stress and consequently a cantilever bending response that can be detected.

Detection of cantilever bending response in case of optical readout is performed, for example, by using serial time multiplexed optical beam method with a single position sensitive detector, although other readouts such as electronic or diffraction can be used. The laser spot (about 100 µm diameter) is aligned onto the free end of each sensor where the accuracy of alignment is confirmed by heating test. The expected precision of laser spot alignment is determined by calculating the bending variation at the maximum bending signals between individual cantilever sensors. Well aligned cantilevers at the maximum bending signals should yield a relative standard deviation of the bending signals of about ≤10%, preferably about ≤5%, between them. Correlating the response signal to the presence or absence of the molecule to be detected includes a first step of calculating the net change in stress, using the mathematical model reported above, and then a second step of associating the net change in stress value to the presence of absence of the molecule and, in case of presence, to the concentration level of the molecule.

The molecule is considered not present in the body fluid when the measured differential stress is equal to about zero, which corresponds to mechanical bending of the cantilever of about zero. As understood by one skilled in the art, the absence of a substance from a solution means that the substance concentration is below the sensitivity of the analysis method. For the present method, a molecule to be detected is considered absent from a body fluid when the concentration of such a molecule is below the current limits of detection in femtomolar quantity.

A molecule is considered present in a body fluid when the compressive stress net signal is $\geq 0.02$ mN m$^{-1}$.

EXAMPLES

Cantilever Metal Coating

Cantilever chips fabricated from Si (100) by IBM Research Laboratory, Rüschlikon, Switzerland were first cleaned with freshly prepared piranha solution (ratio 1:1 $H_2SO_4$ and $H_2O_2$) for 20 min. Arrays were then thoroughly rinsed in deionized water before immersing in the second freshly prepared piranha solution for another 20 min, and again rinsed thoroughly with deionized water. Finally, the arrays were rinsed with pure ethanol and dried on a hotplate at 70° C. for 20 seconds. They were then inspected using the optical microscope to confirm their cleanliness before transferred to the evaporation chamber (BOC Edwards Auto 500, U.K.) for an overnight pumping. One side of the silicon cantilever surface was metalized using an electron beam evaporation with a 2 nm Ti adhesion layer followed by 20 nm of Au at a base pressure of $\sim 3 \times 10^{-7}$ mbar, and at an evaporation rate of 0.02 nm/s for Ti and Au, respectively, as measured directly above the source by a quartz crystal monitor. Once the desired thicknesses were attained, the cantilever chips were left in the chamber for 2-3 hours as described previously to cool under vacuum before removing.

Functionalization of Cantilever Arrays

Case I: Simultaneous functionalization of Au(top) and Si(bottom) surfaces of cantilever arrays: To systematically alter both Au(top) and Si(bottom) surfaces into chemically active sensing layers, the arrays of eight rectangular cantilevers were subjected to surface capture molecules in microcapillary glass tubes (King Precision Glass, Claremont, Calif., USA), arranged according to the cantilever pitch size of 250 µm. The alkanethiols of self-assembled monolayers (SAMs), namely vancomycin susceptible receptor (VSR~0.6 kDa) analogues to bacterial cell wall precursors that present uncrosslinked peptide motifs terminating in the sequence lysine-D-alanine-D-alanine and 'inert' SAM molecule terminating in triethylene glycol (PEG) whose detailed structural sequences have been described previously were diluted in ethanol solution to yield total concentrations of: 0.1 µM, 1 µM, 10 µM, 50 µM, 100 µM, 1000 µM, 2000 µM, 3000 µM and 4000 µM. Individual VSR and PEG concentrations were injected into micro-capillary glass tubes and cantilevers were then incubated inside the capillaries for 20 min, washed three times with ethanol and stored in distilled water until usage. The functionalization procedure was carried out without pre-adsorbing resistive protein monolayer bovine serum albumin (BSA) or PEG-silane, known for blocking nonspecific interactions.

PEG was used as a cantilever reference coating material because of its known properties of minimizing or blocking biomolecular adsorptions (proteins/drugs) on the surfaces.

To tune the receptor footprint (area per each receptor molecule) for enhanced biodetectability and to achieve satisfactory quantitative drug-target measurements, certain steps within the functionalization protocol were addressed. The first task was to define the percentage ratio of VSR by incorporating a receptor molecule with second SAM-forming molecule PEG. The ratio of VSR and PEG molecules dissolved in ethanol was varied to yield a total concentration in the solution of 1 µM, for which full surface coverage was established. The corresponding mixed ethanolic thiol solutions of VSR and 'inert' PEG mixed in the ratio of 30%, 70%, 90%, and 100% were used to coat cantilever arrays.

Functionalization of SPR Sensor Chips with VSR Receptor Molecules

Case II: functionalization of SPR sensor chips with VSR receptor molecules: The plain Au-coated SPR sensor chips were covered with 100 µl ethanolic thiol solutions of VSR and incubated for 20 min to systematically alter a Au-coated surface of the SPR sensor chip into chemically active sensing layer before washing three times with ultrapure ethanol. Binding and affinity experiments were performed on T100 BIAcore SPR Instrument using the same solutions as in the cantilever experiments for the drug-target binding interactions.

Cantilever Si Underside Passivation

Case III cantilever Si underside passivation: The passivation of Si (bottom surface of cantilever) arrays of the eight rectangular cantilever probes was performed using 2-methoxypoly(ethyleneoxy)propyl]trimethoxysilane (7 ethylene glycol units, ABCR, Karlsruhe, Germany) or PEG-silane. This procedure was achieved by incubating freshly functionalized cantilever sensor arrays in a mixture of 3 ml dry ethanol and 15 μl of PEG-silane for 30 min to create a PEG-silane layer on bare silicon under side surface. Next, the percentage ratios of receptors (2B4F and anti-factor (VIII)) was defined and the surface molecular footprints were tuned. A surface linker molecule, (HS-C11-Eg)$_3$-$OCH_2$—COONHS) (ProChimia Surfaces, Poland) where Eg is the ethylene glycol group and NHS is the N-hydroxysuccinimide group, was incorporated with a second SAM-forming molecule PEG (HS-C11-Eg)$_3$-OMe) where Me is the methyl group. The NHS and PEG were diluted in ethanol to yield the percentage ratios of 20%, 60% 80%, 90%, and 100% where the total concentration of the SAMs in the solution was fixed at 2 mM.

The mixed ethanolic thiol solutions of NHS and PEG were subsequently used for the functionalization of cantilever arrays. The freshly coated cantilever arrays with a mixture of NHS and PEG were incubated in sodium acetate buffer solution (5 mM, pH 5.4) for 5 mins to activate the surface for the coupling reaction. The solutions (50-100 μg/ml in sodium phosphate buffer at pH 7.4) of variable domains of 2B4F (~15 kDa) derived from VHH of llama single heavy chain antibodies and anti-Factor (VIII) (~280 kDa) were injected across cantilever arrays and incubated overnight at 4C for coupling reactions to occur at the activated NHS thiolated binding sites. After an overnight incubation, the microarrays were subjected to a 'capping' procedure, using 1 M ethanolamine, pH 8.5 to de-activate unreacted NHS thiols and rinsed thoroughly in PBS buffer at pH 7.4 three times and stored in sodium phosphate buffer at pH 7.4 until usage.

SPR Functionalization with VHH 2B4F Using Carboxymethyl Dextran Matrix (CM5) and Plain Au-Coated SPR Sensor Chips Case IV: SPR sensor chip functionalization with 2B4F antibody: Plain Au-coated SPR sensor chips were coated with 2B4F via NHS thiolated surface linkers. The 2B4F was immobilized on a plain Au-coated SPR sensor chip at 25° C. The procedures involved offline functionalization and online in-situ functionalization to investigate their performance. For the online functionalization, the surface of the Au-coated SPR chip was injected with the mixture of NHS and PEG in the ratio of 9:1 at 2 mM total concentration of both SAMs for 20 min at a flow rate of 5 μl $min^{-1}$. The freshly functionalized SPR sensor chip was activated for 7 min at a flow rate of 5 μl$min^{-1}$ using a 5 mM solution of sodium acetate buffer before the injection of 2B4F diluted in 100 mM sodium phosphate buffer at pH 7.4 to a concentration of 100 μg/ml at a flow rate of 5 μl $min^{-1}$ for 10 mins. The unreacted activated NHS groups were then blocked by using a 7 mins injection of 1 M ethanolamine, pH 8.5, at a flow rate of 5 μl $min^{-1}$. For the offline functionalization, the plain Au-coated SPR chips were incubated with 2B4F solution for 20 min to systematically alter a Au-coated surface of the SPR sensor chip into a chemically active sensing layer before washing three times with ultrapure ethanol. In case of the carboxymethyl dextran matrix (CM5), SPR sensor chip, an online in-situ functionalization was used for all the experiments.

Solutions

Vancomycin and protein solutions: PBS: 0.1 M mono- and di-basic sodium phosphate salts (Sigma-Aldrich, UK) were dissolved in ultrapure water (18.2 MΩ cm 10 resistivity, Millipore Co., Billerica, Mass., U.S.A.) and mixed to yield a pH value of 7.4. The buffer solutions were filtered using 0.2 μM filter (Millipore) and subsequently used to dissolve gp140CN54 (subtype B/C) and gp140UG37 (subtype A). Different concentrations of these HIV-1 isolates were serially diluted from the stock (532 μg/ml).

Characterisation of VSR Using X-Ray Photoelectron Spectroscopy

The surface coverage of VSR was quantified using X-ray photoelectron spectroscopy (XPS), based on the previously reported method. In order to estimate the area of VSR ligand-presenting molecule on the gold substrate, the extensive research that has been done on simple alkanethiol monolayers on gold surface was utilized. For instance, it is well understood that an ideally packed alkanethiol SAM on Au surface yields a packing density of ~0.26 $nm^{-2}$. It is also known from experimental values that a PEG monolayer has a grafting density of ~0.27 $nm^{-2}$ and therefore by comparing the ratio of the S 2p/Au 4f signal of the VSR and PEG reference samples, the surface area per ligand presenting molecule (Table S1) could be calculated.

TABLE S1

The surface area occupied per VSR molecule calculated
from X-ray photoelectron spectroscopy (XPS) data.

| VSR concentration (μM) | Surface area per per VSR Molecule (nm$^2$) |
|---|---|
| 0.1 | 4.65 |
| 1 | 1.59 |
| 10 | 0.65 |
| 50 | 0.54 |
| 100 | 0.55 |
| 1000 | 0.47 |
| 2000 | 0.44 |

The samples containing the lowest concentration of VSR gave the least packing density, with an area of ~4.65 nm$^2$ per VSR molecule, which correspond to a widely dispersed VSR layers. Whereas for highly concentrated samples, it was found that they gave denser packing densities with an area of ~0.44 nm$^2$ per VSR molecule (Table S1). In contrast, for the lower concentrations, the grafting density was found to vary across the range, yielding a dramatic increase in the area per receptor molecule of ~0.54 nm$^2$ per VSR molecule at 50 μM concentration. Additionally, as the VSR concentration was increased further, the packing density was shown to increase rapidly (Table S1).

Finally, to determine which structural features of the surface that regulate the access and insertion of ligand molecules to enhance the efficiency of stress transduction on the cantilever arrays, a mixture of VSR/PEG solutions was prepared with a VSR molar fraction of 0.0, 0.05, 0.1, 0.3, 0.5, 0.7, 0.9 and 1.0 (the ratio of 0.0 indicates pure PEG solution and the ratio of 1.0 represents pure VSR solution). High resolution scans of the N (1s), S (2p) and Au (4f) peaks were recorded using an analyzer pass energy of 20 eV and by referring to the grafting density of 0.27 nm$^{-2}$ per PEG monolayer, the surface area occupied by each VSR molecule in the mixed ratios was calculated. The results are summarized (Table S2).

TABLE S2

The surface area occupied per VSR molecule (diluted
with PEG in solution) calculated from X-ray photoelectron
spectroscopy (XPS) data.

| VSR mole fraction (μM) | Surface area per per VSR Molecule (nm$^2$) |
|---|---|
| 0.0 | ∞ |
| 0.3 | 4.54 |
| 0.5 | 2.20 |
| 0.7 | 1.20 |
| 0.0 | 0.64 |
| 1.0 | 0.44 |

Results

Figure 1B:
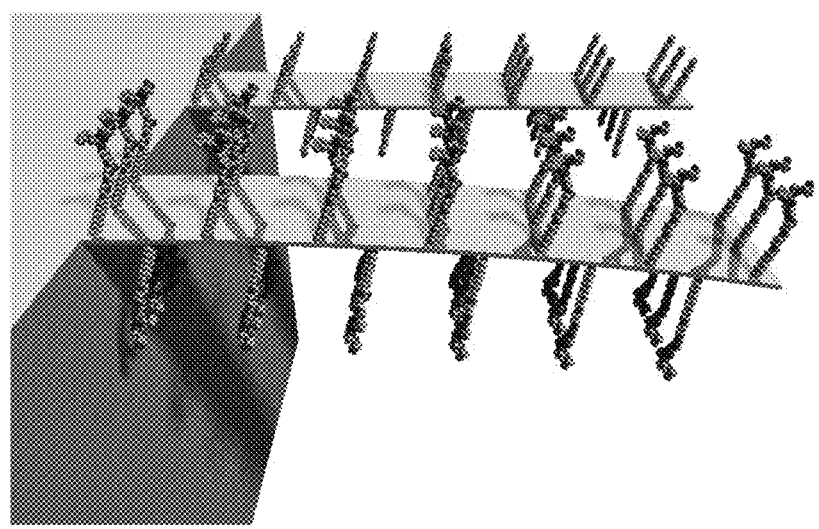

FIG. 1a-b show the functionalization of both surfaces of the cantilever with a self-assembled monolayer (SAM) of vancomycin (Van) susceptible receptor (VSR ~0.6 kDa) analogues of the bacterial cell wall precursors that present uncrosslinked peptide motifs terminating in the sequence lysine-D-alanine-D-alanine. To eliminate the artifacts that produce non-specific signals differential measurements were performed in which reference polyethylene glycol(PEG)-coated cantilever bending signals were subtracted from the receptor signals.

This functionalization was performed without pre-adsorbing a resistive protein monolayer of bovine serum albumin (BSA) or PEG-silane, which are known to block non-specific interactions. Van was used as a reporter molecule because it reacts specifically with VSR to generate stress, which leads to cantilever bending deflections.

Figure 2A:
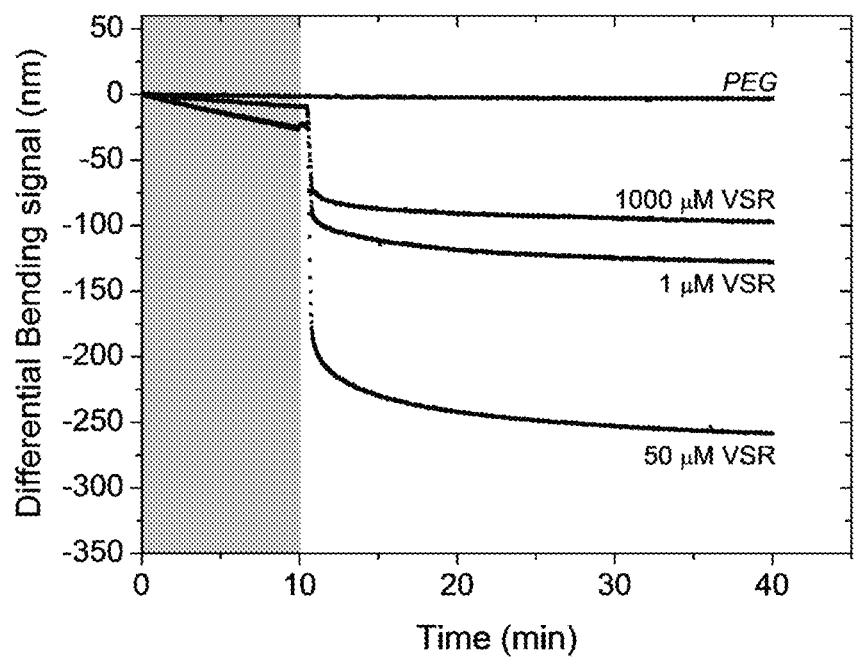
FIG. 2a show the differential cantilever bending signal for 1 μM, 50 μM and 1,000 μM VSR against Van (fixed at 250 μM) to investigate the effect of surface chemistry on stress signaling. The differential PEG reference signal is shown in black. The cantilevers were found to bend downwards due to steric and electrostatic repulsive interactions between bound ligand-receptor complexes.

To probe the stresses due to antibiotic binding to different sensing surfaces, Van was injected onto unpassivated cantilevers functionalized with VSR. The outcome after adding 250 μM Van is summarized in FIG. 2a. The bending response (shown in FIG. 2a) is caused by interactions of Van molecules at the surface, with the formation of a Van-VSR complex that induces a local strain in the cantilever as well as carrying an electrostatic positive charge under a physiologically relevant environment. The electrostatic repulsive and steric interactions between Van-VSR complexes create a compressive stress at the Au surface, causing the cantilevers to bend downwards. The reference PEG-coated cantilevers, as expected, show no bending response against Van. The mechanical response generated by the Van-VSR complex interactions increases with increasing VSR concentration, but decreases at the high concentration of 1,000 μM.

Figure 2B:
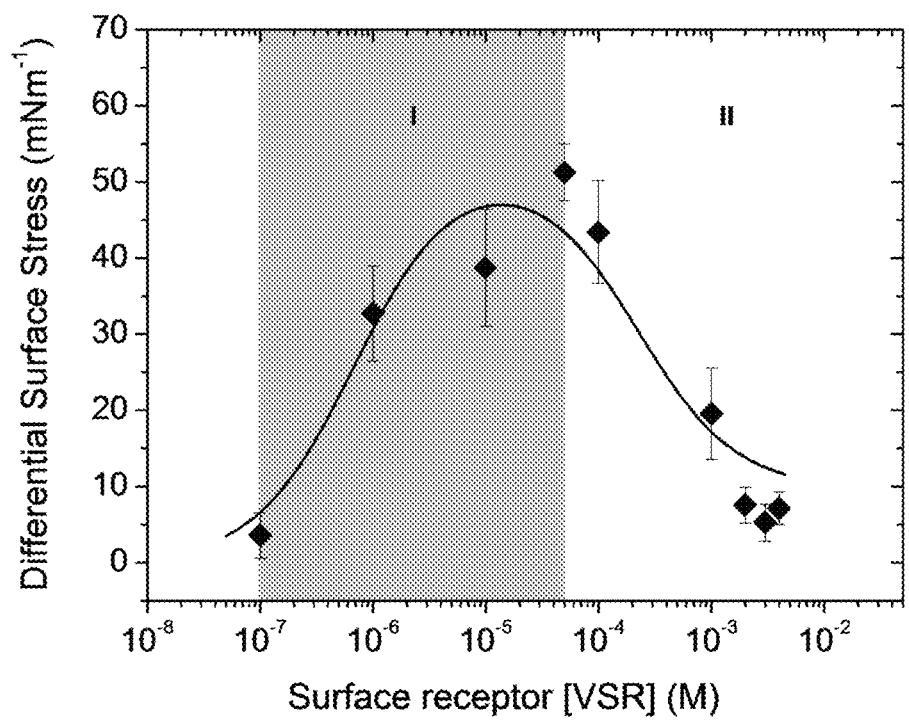
FIG. 2b depicts the semi-logarithmic plot showing measured differential surface stress response as a function of [VSR] in solution against Van (fixed at 250 μM), superimposed on the results of the fit using equation (1) (solid line), derived from formula (1). Regime I for VSR represents the initial stages of the self-assembly of molecules, and regime II has a complete SAM of molecules on both top and bottom cantilever surfaces.

The effect of VSR concentration on signal amplification is summarized in FIG. 2b. The stress response to VSR concentration may be categorized into two regimes (I and II). Regime I represents the initial stages of self-assembly of the molecules and is characterized by a sharp rise in compressive stress up to 52 mN m$^{-1}$, when the concentration of VSR in solution is 50 μM. This is approximately two times more sensitive than previous measurements, where the net stress was measured to be 33 mN m$^{-1}$. However, as the VSR concentration increases beyond 50 μM (regime II), a significant decrease in stress signals down to $\sigma_{max} \approx 5$ mN m$^{-1}$ was found. In contrast, zero differential stress was observed for the reference PEG-coated cantilevers. As a further measurement control uncoated Au and Si surfaces were used. The undetectable mechanical response in the presence of Van is additional verification that the observed deflection signal is caused by the interactions of Van with VSR. In general, the non-monotonic stress signal changes observed in FIG. 2b are not surprising given that the reported SAM formation on Si can give rise to negative contributions to the net cantilever stress signal.

Ligand Sensing Based on Surface Plasmon Resonance

With stress signal reduction at the Au surface occurring at high VSR concentrations (FIG. 2b), the next objective was to confirm that these changes were caused by the opposing Si reactions. Therefore, a commercially available surface plasmon resonance (SPR) method where the detection of biochemicals is at a single planar metal surface was used.

Figure 2C:
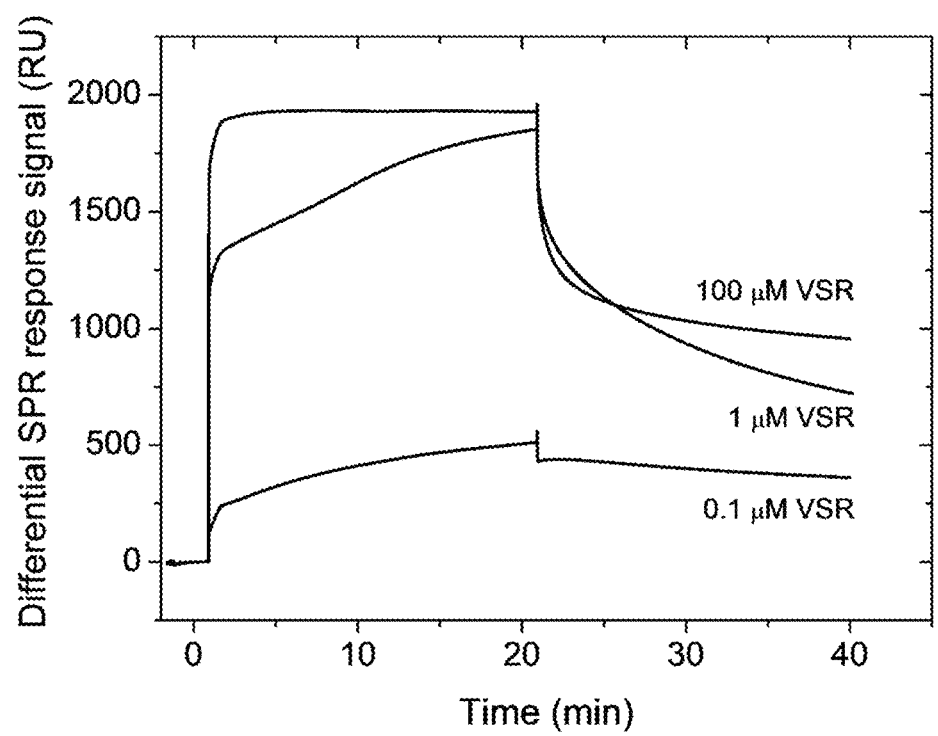
FIG. 2c shows the differential SPR response signals for 0.1 µM, 1 µM and 100 µM VSR against Van (fixed at 250 µM) to investigate the effect of receptor concentration on signal amplification.

SPR detection is based on monitoring changes in the dielectric properties caused by ligand adsorption. Accordingly, a series of binding analyses for VSR was performed, with [Van] kept constant at 250 μM to match the experimental conditions for the cantilever-based measurements. FIG. 2c shows that the differential SPR signal response increases with increasing VSR concentration.

Figure 2D:
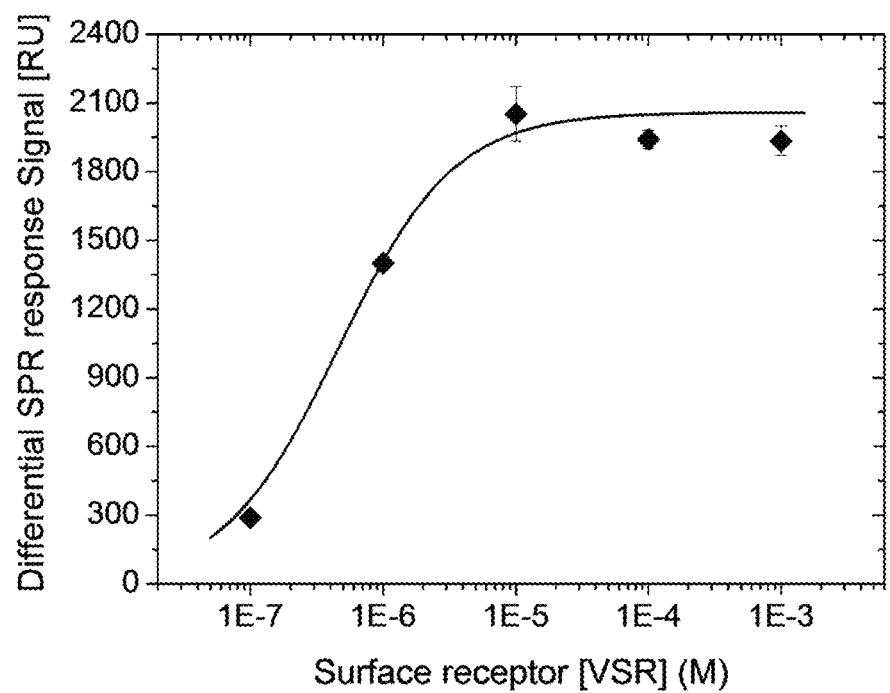
FIG. 2d is the semi-logarithmic plot showing the measured differential SPR response signal as a function of [VSR] in solution against Van concentration (fixed at 250 µM), superimposed on the results of the fit using a mathematical model simulating a cantilever in which there is no free available Si bottom surface (not reported in the disclosure).

The SPR response features an S-shaped curve, with a steep rise, then a plateau when the receptor concentration increases beyond 10 μM (FIG. 2d). The SPR analysis of the signal response versus VSR concentration shown in FIG. 2d remains constant even when [VSR] is extended to 1,000 μM and, when compared with direct mechanical quantitation (FIG. 2b), demonstrates that the reduction of stress signals at higher VSR concentration is linked to Si reactions on the cantilever underside. These measurements provide the first demonstration that the direct functionalization of cantilevers, without underside passivation (FIG. 1a), can be achieved by the effective tuning of receptor concentrations in solution described here. Previous measurements using cantilevers have focused on one side only, but this analysis shows how the underlying Si surface affects the overall mechanical response.

Effect of Receptor Surface Footprint on Ligand Binding

Figure 3:
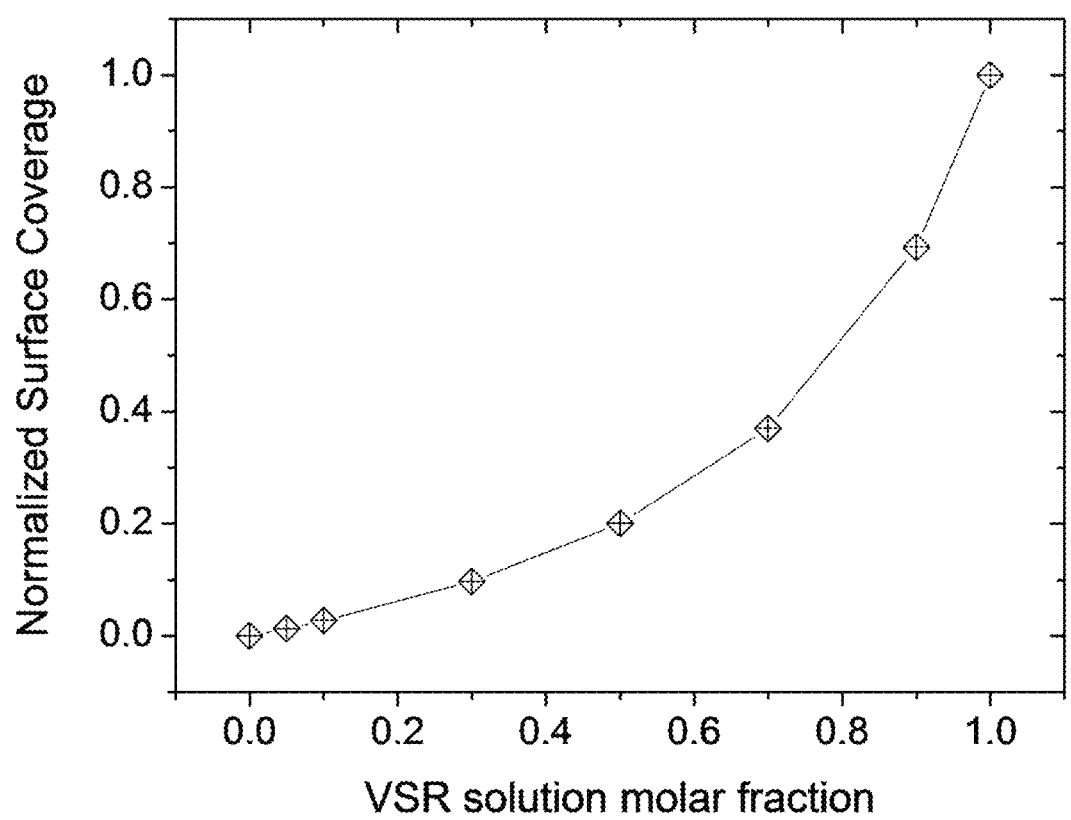
FIG. 3 is a plot showing the measured normalized surface coverage (symbols) obtained using X-ray photoelectron spectroscopy (XPS) as a function of the molar fraction of receptor (diluted with PEG in solution).

Although it is understood that receptor-ligand interactions in solution are linked to stress generation, it is unclear how the surface footprint correlates with the concentration of receptors in solution. The results showing that surface coverage is a function of receptor concentration in solution are summarized in Tables 1 and 2 below and FIG. 3. To study the impact of receptor spacing on stress generation efficiency, a receptor molecule with a second SAM-forming molecule (PEG) was incorporated on the Au surface without underside passivation.

PEG was chosen because it resists the unwanted adsorption of ligands by acting as a protein 'repellent'. Moreover, it acts as a 'spacer' by varying the distribution of receptors on the surface while simultaneously controlling the accessibility of ligands.

Figure 4A:
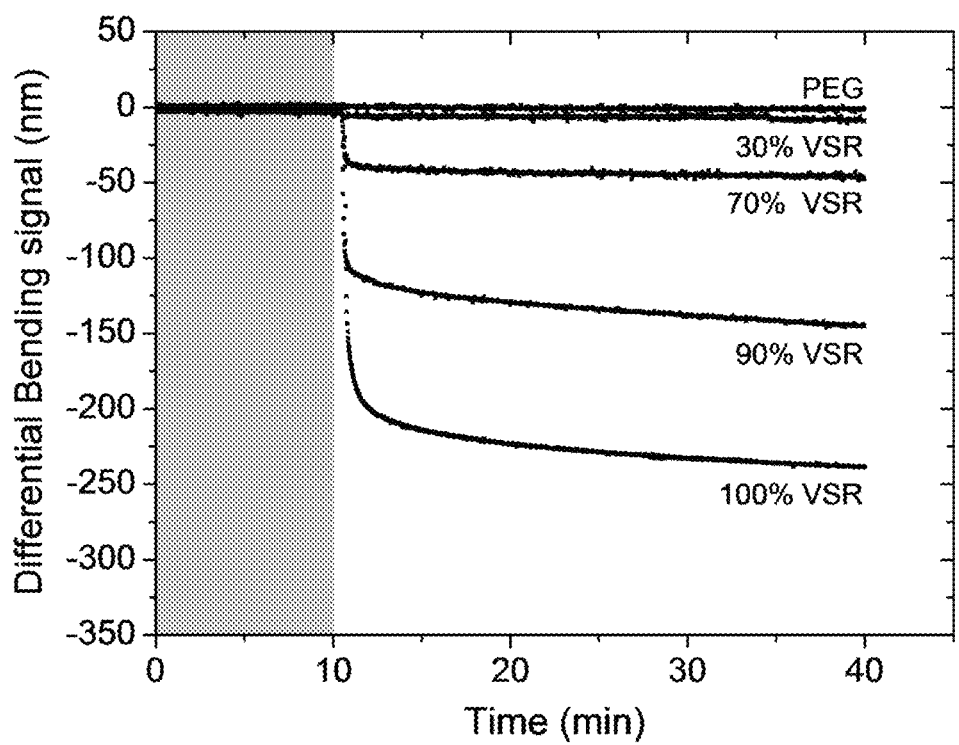
FIG. 4a shows the differential cantilever bending response signals in sodium phosphate buffer solution for defined percentage ratios of 30%, 70%, 90% and 100% VSR (diluted with PEG in solution) fixed at a total receptor solution concentration of 1 µM, at which the net cantilever stress signal contribution from the underlying Si reactions is negligible when exposed against Van at 250 µM. A negative signal corresponds to a compressive surface stress, which results in a cantilever downward-bending deflection.

FIG. 4 shows the outcome when cantilevers were exposed to a constant antibiotic concentration at 250 µM Van with a defined ratio of VSR/PEG, where the total receptor concentration was fixed at 1 µM to minimize the negative impact of Si reactions. With sparsely distributed receptor (~30%) the cantilever deflection signal is negligible. However, when the receptor concentration is increased to 100%, the surface packing density is maximized and yields the highest stress (FIG. 4). These actions show that the number of ligand-receptor interactions increases with coverage, although there is a threshold in the surface footprint to generate a mechanical response, in good agreement with previous studies.

Figure 4B:
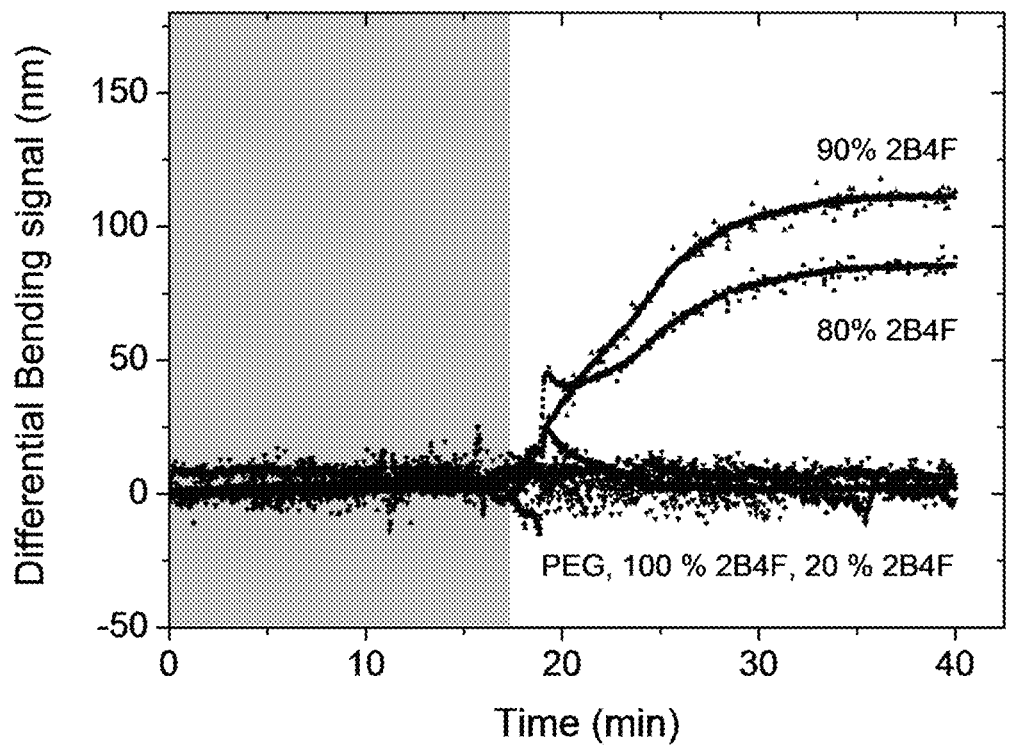
FIG. 4b shows a schematic representation of the coupling approach. Receptor molecules (Y shape) covalently bind to Au (top) surface via thiol groups that are created through the modification of reactive N-hydroxysuccinimide (NHS) ester groups with primary amines. SAM terminating with PEG or OMe were incorporated between the receptors in a defined ratio to enhance the biospecific binding efficiency of the sensing layer by reducing non-specific binding on the Au surface. Passivation of the cantilever Si surface was achieved using PEG-silane to block a non-specific underside reaction.

To examine the impact of coverage on signal amplification and to exclude any possibilities of the contributions from Si reactions, the cantilever underside was passivated. To provide insight into the dependence of stress generation on molecular size, testing was performed on the N-terminal fragment (VHH) of llama single chain antibodies 36 that have a molecular weight of about 15 kDa, some 25× larger than VSR but only 10% of a conventional immunoglobulin. VHH are stable over a broad temperature range (−80° C. to 80° C.) and are inexpensive to manufacture with excellent expression yields from bacteriophage libraries. VHH raised against the human immuno-deficiency virus (HIV-1) trimeric envelope glycoprotein (gp140), as previously described, was chosen. One VHH, termed 2B4F, was chosen because of its high specificity and sensitivity of binding to the gp140 by SPR. FIG. 4b shows the outcome after exposure to recombinant antigens derived from HIV-1 subtype A (gp140UG37, 140 kDa) fixed at 50 µM against a defined percentage ratio of 2B4F/PEG, where the total concentration was fixed at 2 mM.

The observed noise was probably caused by laser light scattering by the proteins. The response signal was not detectable at 20% relative concentration, but increased as the concentration was increased between 80 to 90%. Surprisingly, 100% receptor concentration in solution was found to yield insignificant stress signals. Generally, these findings reveal that the efficiency of stress generation for proteins is strongly dependent on the surface molecular footprint. In contrast, for small molecules such as Van (~1.4 kDa), the stress is maximized when the receptor packing densities is highest.

We claim:

1. An unpassivated cantilever sensor having two sides comprising a polyamide or silicon layer coated on one side with a coating comprising at least a gold layer and being uncoated or unpassivated on the opposite side,
wherein both sides of the cantilever are functionalized with a self-assembled monolayer (SAM) of a probe molecule bound to a linker, and
wherein the surface area occupied per probe molecule on the gold layer coated surface ranges from about 0.4 to about 1.5 nm$^2$.

2. The unpassivated cantilever of claim 1, wherein the coating comprising at least a gold layer is a coating comprising a base titanium layer and a top gold layer.

3. The unpassivated cantilever of claim 2, wherein the thickness of the titanium layer is between 1 and 5 nm.

4. The unpassivated cantilever of claim 2, wherein the thickness of the gold layer is between about 5 and about 50 nm.

5. The unpassivated cantilever of claim 2, wherein the thickness of the gold layer is between about 10 and about 20 nm.

6. The unpassivated cantilever of claim 1, wherein the self-assembled monolayer is an alkanethiol self-assembled monolayer in which the alkanethiol moiety is the linker between the probe molecule and the gold and/or any other material including silicon surface of the cantilever.

7. The unpassivated cantilever of claim 6, wherein the alkanethiol linker is an alkanethiol polyethylene glycol linker.

8. The unpassivated cantilever of claim 6, wherein the alkanethiol linker is $HS(C_{8-15})alkyl-(OCH_2CH_2)_nOH$, wherein n=2-5.

9. The unpassivated cantilever of claim 6, wherein the alkanethiol linker is $HS(C_{8-15})alkyl-(OCH_2CH_2)_3OH$, that binds to the gold and/or any other material including silicon surface of the cantilever via the —SH residue and binds to the probe molecule via an —OH group on the probe molecule.

10. The unpassivated cantilever of claim 1, wherein the probe molecule is a molecule able to interact with specificity and sensitivity with a coupling molecule to generate ligand-receptor interactions, drug-receptor interactions, antibody-antigen interactions, sequence-specific DNA interactions, RNA hybridization-type interactions, or combinations thereof.

11. The unpassivated cantilever of claim 1, wherein the probe molecule is a receptor able to provide ligand-receptor or drug-receptor binding; a probe molecule able to selectively hybridize to a complementary DNA or RNA sequence; or an antibody able to provide antibody-antigen interactions.

12. The unpassivated cantilever of claim 10, wherein the probe molecule is a vancomycin susceptible receptor (VSR), a monoclonal human immunodeficiency virus antibody (anti-p24), a blood clotting factor (VIII) antibody (anti-Factor(VIII)), or a polyclonal anti-prostate-specific antibody (anti-PSA).

13. The unpassivated cantilever of claim 1, wherein the surface area occupied per probe molecule ranges from about 0.5 to about 0.6 nm$^2$.

14. The unpassivated cantilever of claim 1, wherein the surface area occupied per probe molecule ranges from about 0.6 to about 1.2 nm$^2$.

15. An array comprising at least 8 unpassivated cantilever sensors, each unpassivated cantilever sensor according to claim 1.

16. A method for detecting the presence of a coupling molecule in an isolated body fluid, comprising the steps of:

1) providing an unpassivated cantilever sensor according to claim 1;
2) contacting the cantilever sensor with an isolated body fluid containing the coupling molecule to be detected;
3) detecting the response signal due to cantilever bending; and
4) correlating the response signal to the presence or absence of the coupling molecule to be detected.

17. The method according to claim 16, wherein the body fluid is blood, plasma, saliva, sputum, or urine.

18. The method according to claim 16, wherein the coupling molecule is a ligand, a drug molecule, an antigen or a hybridizing nucleic acid sequence.

19. The method of claim 18, wherein the coupling molecules is vancomycin, glycoprotein p24, factor (VIII), or prostate specific antigen (PSA).

20. The method of claim 16, wherein the contacting step is performed for a period of 5-30 minutes.

21. The method of claim 16, further comprising the step of correlating the response signal to the concentration of the coupling molecule in solution.

\* \* \* \* \*